(12) United States Patent
Rosado

(10) Patent No.: US 8,257,339 B1
(45) Date of Patent: Sep. 4, 2012

(54) PNEUMOTHORAX RELIEF VALVE METHOD

(76) Inventor: Manuel T. Rosado, Jacksonville, FL (US)

( * ) Notice: Subject to any disclaimer, the term of this patent is extended or adjusted under 35 U.S.C. 154(b) by 407 days.

(21) Appl. No.: 12/459,294

(22) Filed: Jun. 30, 2009

Related U.S. Application Data

(63) Continuation-in-part of application No. 11/708,435, filed on Feb. 20, 2007, now abandoned.

(51) Int. Cl.
*A61M 31/00* (2006.01)
(52) U.S. Cl. .................................................. 604/506
(58) Field of Classification Search ............. 604/164.01, 604/164.07, 164.08, 170.02, 161, 506
See application file for complete search history.

(56) References Cited

U.S. PATENT DOCUMENTS

| | | | |
|---|---|---|---|
| 4,153,058 A * | 5/1979 | Nehme | 604/167.03 |
| 4,813,941 A | 3/1989 | Shea | |
| 5,181,913 A | 1/1993 | Erlich | |
| 5,419,776 A | 5/1995 | Baer | |
| 6,402,770 B1 * | 6/2002 | Jessen | 606/170 |

* cited by examiner

*Primary Examiner* — Kevin C Sirmons
*Assistant Examiner* — Bradley Osinski

(57) ABSTRACT

An operative member has a cylindrical catheter, an essentially cylindrical hub, an interior passageway and a roll out, open ended flutter valve. The valve has a fixed end secured to the hub and an extendable end. A needle has a stylet distal end and a proximal end formed with a gripping handle. The needle is adapted to be removably positioned within the interior passageway of the catheter and hub. The distance between the handle and the distal end of the needle is slightly greater than the length of the catheter and the hub. After providing the components set forth above, the present invention includes the step of inserting the catheter and needle into a pleural space of a patient and then withdrawing the needle thereby creating an air passageway through the catheter and the catheter and then unrolling the flutter valve from the hub.

1 Claim, 4 Drawing Sheets

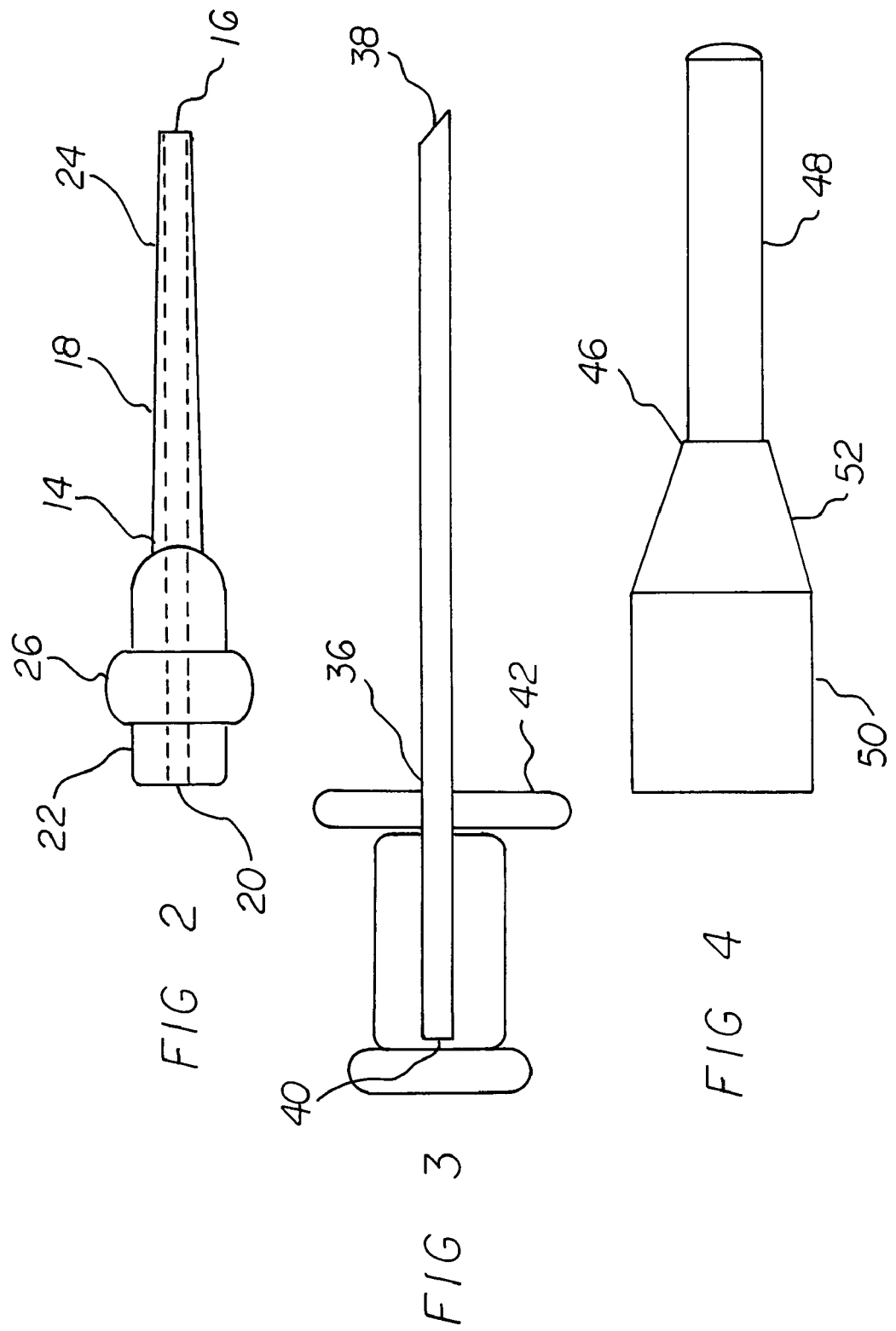

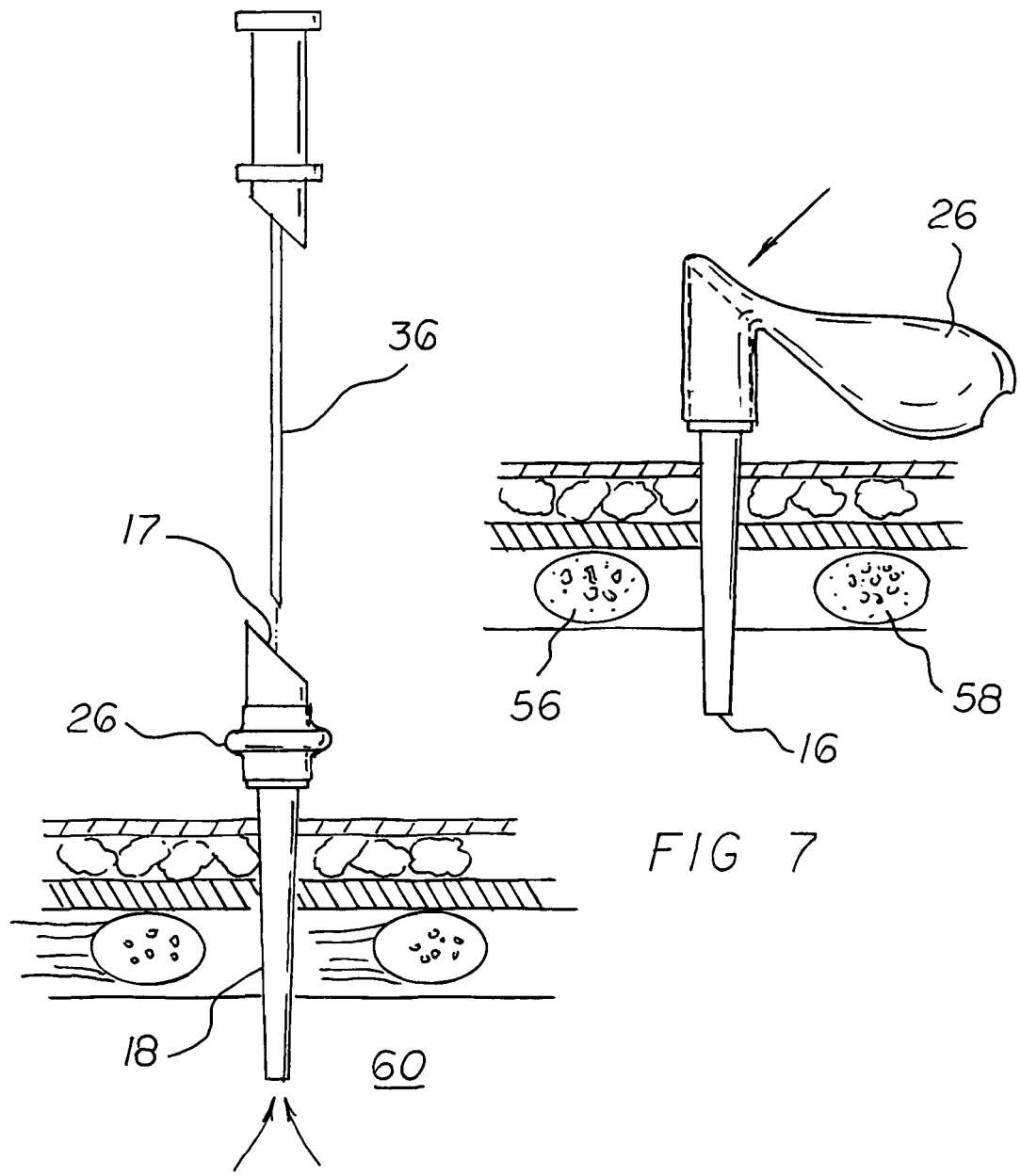

PNEUMOTHORAX RELIEF VALVE METHOD

RELATED APPLICATION

The present patent application is a continuation-in-part of U.S. patent application Ser. No. 11/708,435 filed Feb. 20, 2007, now abandoned the subject matter of which is incorporated herein by reference.

BACKGROUND OF THE INVENTION

1. Field of the Invention

The present invention relates to a hemothorax/pneumothorax relief valve method and more particularly pertains to allowing the passage of high pressure air from a pleural cavity while precluding the passage of air and, on occasion, blood into such pleural cavity in a safe, rapid and economical manner. By hemothorax/pneumothorax it is meant hemothorax alone or pneumothorax alone or hemothorax and pneumothorax together.

2. Description of the Prior Art

The use of hemothorax/pneumothorax relief valve methods of known designs and configurations is known in the prior art. More specifically, hemothorax/pneumothorax relief valve methods of known designs and configurations previously devised and utilized for the purpose of treating chest wounds are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,813,941 issued Mar. 21, 1993 to Shea relates to a Pneumothorex Treatment Device. U.S. Pat. No. 5,181,913 issued Jan. 26, 1993 to Erlich relates to a Catheter with Check Valve and Rolled Sheath. Lastly, U.S. Pat. No. 5,419,776 issued May 30, 1995 to Baer relates to a Pneumothorex Treatment Device.

While these devices fulfill their respective, particular objectives and requirements, the aforementioned patents do not describe a hemothorax/pneumothorax relief valve method that allows the passage of air and blood from a pleural cavity while precluding the passage of air and blood into such pleural cavity in a safe, rapid and economical manner.

In this respect, the hemothorax/pneumothorax relief valve method according to the present invention substantially departs from the conventional concepts and designs of the prior art, and in doing so provides an apparatus primarily developed for the purpose of allowing the passage of air and blood from a pleural cavity while precluding the passage of air and blood into such pleural cavity in a safe, rapid and economical manner.

Therefore, it can be appreciated that there exists a continuing need for a new and improved hemothorax/pneumothorax relief valve method which can be used for allowing the passage of air and blood from a pleural cavity while precluding the passage of air and blood into such pleural cavity in a safe, rapid and economical manner. In this regard, the present invention substantially fulfills this need.

SUMMARY OF THE INVENTION

In view of the foregoing disadvantages inherent in the known types of hemothorax/pneumothorax relief valve methods of known designs and configurations now present in the prior art, the present invention provides an improved hemothorax/pneumothorax relief valve method. As such, the general purpose of the present invention, which will be described subsequently in greater detail, is to provide a new and improved hemothorax/pneumothorax relief valve method which has all the advantages of the prior art and none of the disadvantages.

To attain this, the present invention essentially comprises a hemothorax/pneumothorax relief valve method. First provided is an operative member. The operative member has a distal end. The operative member has a cylindrical catheter. The catheter is fabricated of a surgical plastic. The operative member has a proximal end. The operative member has an essentially cylindrical hub. The hub is fabricated of a rigid plastic material. The catheter and the hub have an interior axial cylindrical passageway along the entire length of the catheter and hub. The proximal end of the hub is open and is located in a plane at an angle of about 45 degrees with respect to an imaginary plane extending perpendicularly through the axis of the catheter and the hub. In this manner air may pass there through. The hub has an exterior diameter. The exterior diameter is between about 2 and 5 times greater than that of the exterior diameter of the catheter.

The operative member also includes a roll out, open ended flutter valve. The operative member has a fixed end. The fixed end is secured to the exterior diameter of the hub. The operative member has an extendable end. The roll out, open ended flutter valve is adapted to be configured between an inoperative orientation rolled up on the hub and an operative orientation unrolled from the hub. In this manner air may pass from a pleural cavity while precluding the passage of air and blood into such pleural cavity. The catheter is slightly, a one millimeter, shorter than the needle and is tapered proximally to the needle stylet.

A needle is provided. The needle is fabricated of a surgical steel. The needle has an exterior cylindrical surface. The needle has a common diameter and a common linear axis of about 2.5 inches along its entire length. The needle is adapted to be removably positioned within the interior passageway of the catheter and hub. The needle has a pointed distal end forming a stylet.

The needle has a proximal end. The proximal end is formed with a gripping handle. The gripping handle is fabricated of a rigid plastic material. The gripping handle has a diameter greater than that of the hub. The distance between the handle and the tip of the needle is greater than the length of the catheter and the hub. The needle is within the operative member. The stylet distal end of the needle and the tapered catheter form a continuous exterior surface. In this manner the chest of a patient may be pierced so that the needle and operative member are inserted and the needle then removed. The catheter is operatively positioned inside a patient and the hub and one way, roll out, open ended, flutter valve are outside the patient.

Provided last is a cap. The cap is fabricated of a transparent plastic material. The cap has a cylindrical distal section. The distal section is of a reduced diameter and a length to encompass a minor portion of the needle and a major portion of the catheter. The cap has a cylindrical proximal section. The proximal section is of an enlarged diameter and a length to encompass a major portion of the hub and a minor portion of the needle adjacent to the handle in abutment with the handle. The cap has a conical section. The conical section couples the proximal and distal sections encompassing portions of the needle and the hub and the catheter.

After providing the components set forth above, the method of the present invention includes additional steps. With the needle positioned within the catheter, and the distal end of the needle extending beyond the distal end of the catheter, the next step is inserting the catheter between the second and third rib of a patient suffering from a tension hemothorax/pneumothorax until the distal end of the catheter is in the pleural space.

The next step in the method is withdrawing the needle from the catheter thereby creating an air passageway between the distal end of the catheter and proximal end of the catheter.

The final method step is unrolling the flutter valve from the hub whereby, when there is no positive air pressure at the distal end of the catheter, the proximal end of the catheter will be covered by the flutter valve at an angle of about 45 degrees with respect to an imaginary plane perpendicular to the axis of the catheter to preclude the escape of air and blood through the catheter; and, whereby when there is positive air pressure at the distal end of the catheter there will be a passageway for air from the distal end of the catheter through the catheter and through the flutter valve to allow the escape of air and blood through the catheter and through the flutter valve.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods for carrying out the several purposes of the present invention. It is important, therefore, that the claims be regarded as including such equivalent constructions insofar as they do not depart from the spirit and scope of the present invention.

It is therefore an object of the present invention to provide a new and improved hemothorax/pneumothorax relief valve method which has all of the advantages of the prior art hemothorax/pneumothorax relief valve methods of known designs and configurations and none of the disadvantages.

It is another object of the present invention to provide a new and improved hemothorax/pneumothorax relief valve method which may be easily and efficiently manufactured and marketed.

It is a further object of the present invention to provide a new and improved hemothorax/pneumothorax relief valve method which is of durable and reliable constructions.

An even further object of the present invention is to provide a new and improved hemothorax/pneumothorax relief valve method which is susceptible of a low cost of manufacture with regard to both materials and labor, and which accordingly is then susceptible of low prices of sale to the consuming public, thereby making such hemothorax/pneumothorax relief valve method economically available. The invention saves time and money.

Even still another object of the present invention is to provide a hemothorax/pneumothorax relief valve method for allowing the passage of high pressure air from a pleural cavity while precluding the passage of air and blood into such pleural cavity in a safe, rapid and economical manner.

Another object of the present invention is to provide a hemothorax/pneumothorax relief valve method which allows emergency personnel to quickly and efficiently treat the emergency situation of a hemothorax/pneumothorax patient and go on to attend to other casualties, thereby saving lives, time and money.

Lastly, it is an object of the present invention to provide a new and improved hemothorax/pneumothorax relief valve method. An operative member has a cylindrical catheter. The operative member has an essentially cylindrical hub and an interior passageway. The operative member also includes a roll out, open ended flutter valve. The valve has a fixed end and an extendable end. The fixed end is secured to the hub. A needle is adapted to be removably positioned within the interior passageway of the catheter and hub. The needle has a pointed distal end constituting a tip or stylet and a proximal end. The proximal end is formed with a gripping handle. The distance between the handle and the tip of the needle is greater than the length of the catheter and the hub. After providing the components set forth above, the present invention includes the step of inserting the catheter and needle into a pleural space of a patient and then withdrawing the needle thereby creating an air passageway through the catheter and then unrolling the flutter valve from the hub.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a side perspective view of the catheter, hub and roll out, open ended flutter valve as shown in FIG. 1.

FIG. 3 is a side perspective view of the needle as shown in FIG. 1.

FIG. 4 is a side perspective view of the cap as shown in FIG. 1.

FIG. 6 is a cross sectional view of the catheter inserted into a patient after removal of the needle and with the flutter valve rolled up on the hub.

FIG. 7 is a cross sectional view of the catheter inserted into a patient and with the flutter valve rolled out from the hub.

The same reference numerals refer to the same parts throughout the various Figures.

DESCRIPTION OF THE PREFERRED EMBODIMENT

Figure 1:
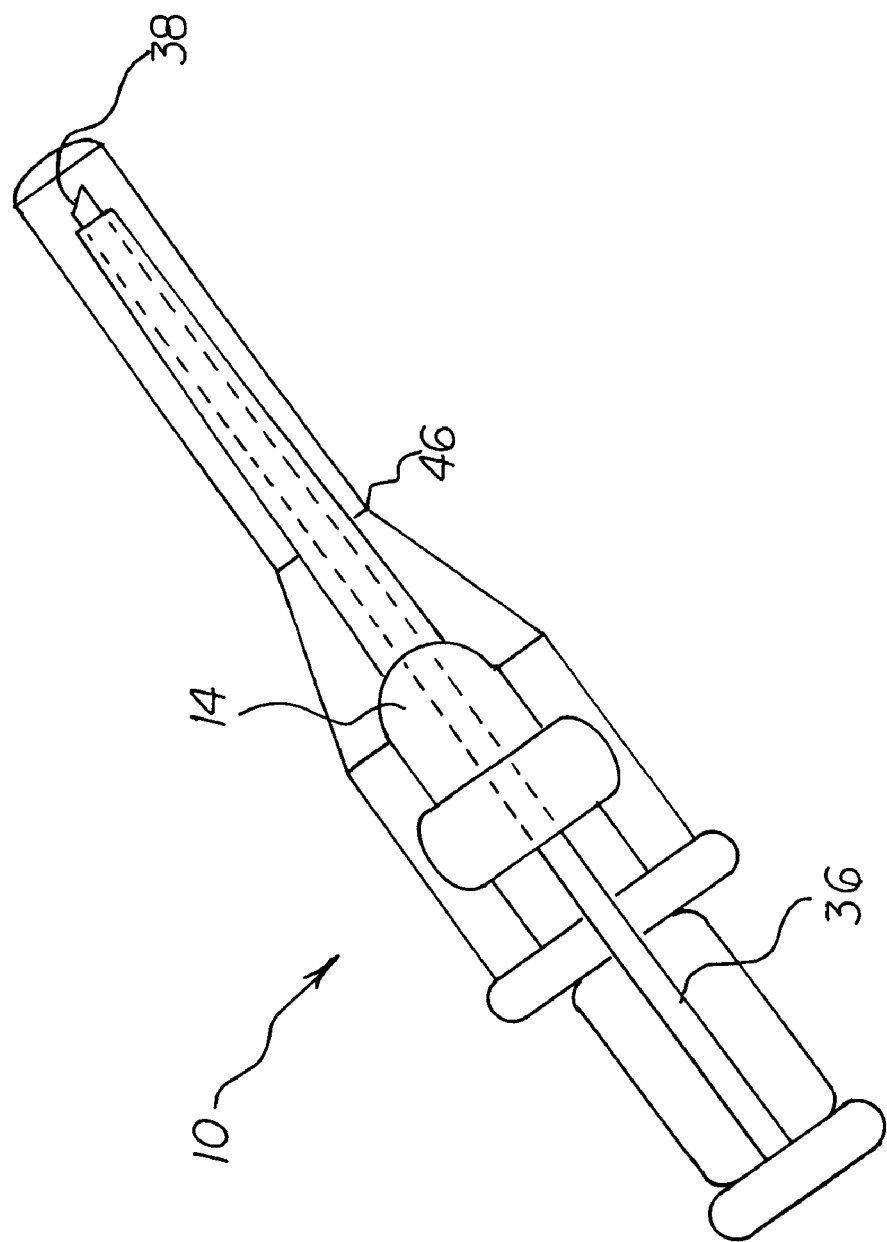
FIG. 1 is a side elevational view of a hemothorax/pneumothorax relief valve method constructed in accordance with the principles of the present invention.
Figure 5:
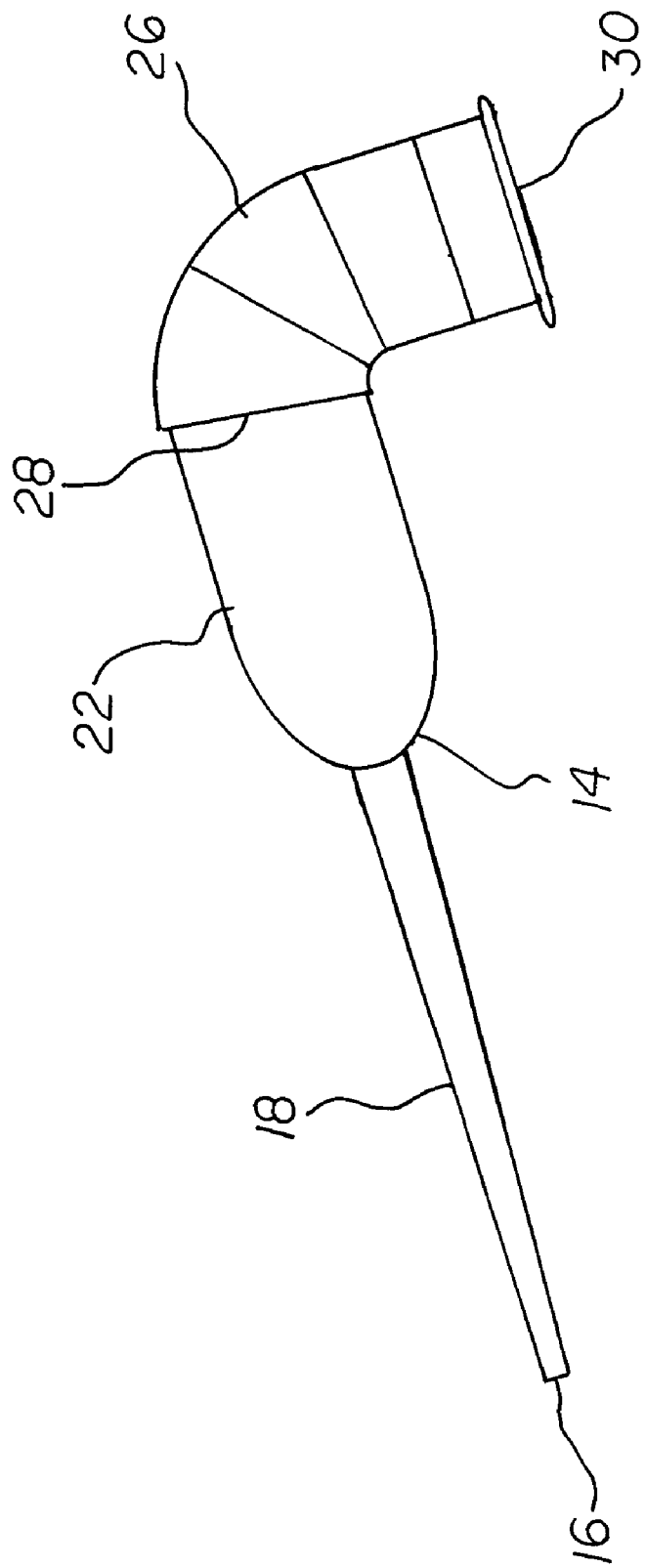
FIG. 5 is a side perspective view similar to FIG. 2 but with the roll out, open ended flutter valve in an extended orientation ready for use.

With reference now to the drawings, and in particular to FIG. 1 thereof, the preferred embodiment of the new and improved hemothorax/pneumothorax relief valve method embodying the principles and concepts of the present invention and generally designated by the reference numeral 10 will be described.

The present invention, the hemothorax/pneumothorax relief valve method 10 is comprised of a plurality of components. Such components in their broadest context include an operative member and a needle. Such components are individually configured and correlated with respect to each other so as to attain the desired objective.

First provided is an operative member 14. The operative member has a distal end 16. The operative member has a cylindrical catheter 18. The catheter is fabricated of a surgical plastic. The operative member has a proximal end 20. The operative member has an essentially cylindrical hub 22. The hub is fabricated of a rigid plastic material. The catheter and the hub have a common interior passageway 24. The proximal end 17 of the hub is open and is located in a plane at an angle of about 45 degrees with respect to an imaginary plane extending perpendicularly through the axis of the catheter and the hub. In this manner air may pass there through. The hub has an exterior diameter. The exterior diameter is between about 2 and 5 times greater than that of the exterior diameter of the catheter.

The operative member also includes a roll out, open ended flutter valve 26. The operative member has a fixed end 28. The fixed end is secured to the exterior diameter of the hub. The operative member has an extendable end 30. The roll out, open ended flutter valve is adapted to be configured between an inoperative orientation rolled up on the hub and an operative orientation unrolled from the hub. In this manner air may pass from a pleural cavity while precluding the passage of air and blood into such pleural cavity. The catheter is tapered becoming gradually smaller toward the distal end.

The roll out one-way valve is preferably formed of a tube of elastomeric material. The interior end is coupled to the hub and will remain open for ensuring the flow of air and blood outwardly from the patient. The exterior end is free and will be rolled out and lie flat, closed upon itself, except when air flows outwardly, not inwardly. Any of a wide variety of materials may be utilized. Acceptable materials include latex, silicone, and also non-latex for people who are allergic to latex.

A needle 36 is provided. The needle is fabricated of a surgical steel. The needle has an exterior cylindrical surface. The needle has a common diameter and a common linear axis of about 2.5 inches along its entire length. The needle is adapted to be removably positioned within the interior passageway of the catheter and hub. The needle has a pointed distal end 38 constituting a stylet.

The needle has a proximal end 40. The proximal end is formed with a gripping handle 42. The gripping handle is fabricated of a rigid plastic material. The gripping handle has a diameter greater than that of the hub. The distance between the handle and the tip of the needle is greater than the length of the catheter and the hub. The needle is within the operative member. In this manner the chest of a patient may be pierced so that the needle and operative member are inserted and the needle is then removed. In this manner the catheter is operatively positioned inside a patient and the hub and one way, roll out, open ended, flutter valve are outside of the patient.

Provided last is a cap 46. The cap is fabricated of a transparent plastic material. The cap has a cylindrical distal section 48. The distal section is of a reduced diameter and a length to encompass a minor portion of the needle and a major portion of the catheter when coupled. The cap has a cylindrical proximal section 50. The proximal section is of an enlarged diameter and a length to encompass a major portion of the hub and a minor portion of the needle adjacent to the handle in abutment with the handle. The cap has a conical section 52. The conical section couples the proximal and distal sections encompassing portions of the needle and the hub and the catheter.

After providing the components as set forth above, the method of the present invention includes additional steps. With the needle positioned within the catheter, and the distal end of the needle extending beyond the distal end of the catheter, the next step of the method of the present invention is inserting the catheter between a second rib 56 and a third rib 58 of a patient suffering from a tension hemothorax/pneumothorax until the distal end of the catheter is in the pleural space 60. The next step is withdrawing the needle from the catheter thereby creating an air passageway between the distal end of the catheter and proximal end of the catheter. The final step is unrolling the flutter valve from the hub whereby, when there is no positive air pressure at the distal end of the catheter, the proximal end of the catheter will be covered by the flutter valve at an angle of about 45 degrees with respect to an imaginary plane perpendicular to the axis of the catheter to preclude the escape of air and blood through the catheter; and, whereby when there is positive air pressure at the distal end of the catheter there will be a passageway for air from the distal end of the catheter through the catheter and through the flutter valve to allow the escape of air and blood through the catheter and through the flutter valve.

In simple terms, the present invention is a two component method. The first component is a 14 gauge, large gauge, 2.5 inch needle. The second component is a catheter and hub with a roll-out flutter valve. The device is used to treat a tension hemothorax/pneumothorax. After the needle and catheter are inserted into the patient's chest, the needle is withdrawn and the catheter and roll-out flutter valve stay in place. The flutter valve is then rolled out to act as a one-way valve. The roll-out flutter valve allows the pressurized air within the pleural cavity to escape but collapses against the hub face preventing air from entering the pleural cavity.

It is considered that tension hemothorax/pneumothorax is the cause of about 33 percent of preventable combat deaths. An injured chest or lung acts as a one-way valve and may occur in an open or a closed chest wound. With such wound, air becomes trapped between the lung and chest wall causing the lung to collapse. The heart is then pushed to one side causing blood vessels to kink. Death results if the tension hemothorax/pneumothorax is not quickly recognized and treated with needle decompression.

Diagnosis of tension hemothorax/pneumothorax should first be made when significant respiratory distress develops in the setting of torso trauma. The diagnosis of tension hemothorax/pneumothorax on the battlefield should not rely on such typical clinical signs as decreased breath sounds, tracheal deviation, or hyper-resonance to percussion because these signs may not always be present and even if they are, they may be exceedingly difficult to appreciate on the battlefield. A patient with penetrating chest trauma will generally have some degree of hemothorax/pneumothorax as a result of his primary wound, and the additional trauma caused by a needle thoracostomy would not be expected to significantly worsen his condition should he not actually have a tension hemothorax/pneumothorax. Paramedics are authorized to perform needle thoracentesis in some civilian emergency medical services. Combat corpsmen and medics should also be proficient in this technique. Chest tubes are not recommended in this phase of care because they are not needed to provide initial treatment for a tension hemothorax/pneumothorax. Chest tubes are more difficult and time-consuming for relatively inexperienced medical personnel especially in the austere battlefield environment. Chest tube insertion is probably more likely to cause additional tissue damage and subsequent infection than needle thoracostomy. No documentation of benefit from battlefield tube thoracostomy by paramedical personnel has been found in literature. Tube thoracostomy is generally not part of the paramedic's scope of care in civilian EMS settings and no studies were found that address the use of this procedure by corpsmen and medics in combat settings.

Needle thoracentesis with a 14-gauge needle was found to rapidly relieve elevated intrapleural pressure in a swine model of traumatic tension pneumothroax. The therapeutic effect was sustained for 4 hours and this procedure was found to be equivalent to tube thoractostomy with a 32F chest tube for the observation period. The ease and speed of performance and the decreased likelihood of complications made needle thoracentesis the procedure of choice for relieving tension pneumothroax on the battlefield. Cannula length is an important consideration here, as the pectoral muscles must be penetrated, and in young soldiers, they can be very thick. Even though it may be difficult to appreciate in field settings, if there is no rush of air and blood when the needle is inserted, then either it did not go in far enough, or there was no tension hemothorax/pneumothorax there. Medics of the 7th Ranger Regiment currently pack 10 ga 3-inch needle/catheters for this procedure. Any patient who has undergone needle thoracentesis for relief of tension hemothorax/pneumothorax must be continually reassessed. Catheters used for this purpose are subject to occlusion by clotting and kinking.

An open hemothorax/pneumothorax, sucking chest wound, may result from large defects in the chest wall and may interfere with respiration. These wounds are treated by applying a vaseline gauze during expiration, covering the gauze with tape or a field dressing, placing the casualty in the sitting position and monitoring for the possible development of a tension hemothorax/pneumothorax.

A collection of air and blood in the pleural space causes loss of the negative pressure that binds the lung to the chest wall. With each breath, the volume of air and blood and pressure within the pleural space increases causing the affected lung to collapse and separate from the thorax. Needle decompression is needed to relieve the high pressure within the pleural space. To use the present invention, first separate the needle, catheter and hub and roll out, open ended flutter valve from its clear sterile plastic cover. Next, locate the insertion point on the mid-clavicular line and advance the needle catheter between the 2nd and 3rd rib. Assure that you pass through the intercostal muscle and enter the thoracic cavity. As the pleural space is entered, a pop or a decrease in resistance is felt. The catheter is then advanced into the chest and the needle withdrawn. The catheter is then secured in place with tape and the flutter valve is unrolled. The silicone like material is flexible enough to allow the high pressure air within the pleural space to escape and also act as a one-way valve and collapse against the hub face to inhibit air form returning into the patient's affected lung via the catheter.

This invention frees up emergency personnel to attend to other casualties. The invention saves lives, time and money.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pneumothorax relief valve method for allowing the passage of air from a pleural cavity while precluding the passage of air into such pleural cavity in a safe, rapid and economical manner comprising, in combination:

providing an operative member having a distal end with a cylindrical catheter fabricated of a surgical plastic and a proximal end with an essentially cylindrical hub fabricated of a rigid plastic material, the catheter and the hub having an axial cylindrical interior passageway for the passage of air there through, the hub having an exterior diameter between about 2 and 5 times greater than that of the exterior diameter of the catheter, the proximal end of the hub being open and located in a plane at an angle of about 45 degrees with respect to an imaginary plane extending perpendicularly through the axis of the catheter and the hub, the operative member also including a roll out, open ended flutter valve with a fixed end secured to the exterior diameter of the hub and an extendable end, the roll out, open ended flutter valve adapted to be configured between an inoperative orientation rolled up on the hub and an operative orientation unrolled from the hub for allowing the passage of air from a pleural cavity while precluding the passage of air to such pleural cavity, the catheter being tapered and larger at the proximal end than the distal end;

providing a needle fabricated of a surgical steel and having an exterior cylindrical surface with a common diameter and a common linear axis of about 2.5 inches along its entire length adapted to be removably positioned within the interior passageway of the catheter and hub, the needle having a stylet distal end and a proximal end formed with a gripping handle fabricated of a rigid plastic material and of a diameter greater than that of the hub, the distance between the handle and the tip of the needle being greater than the length of the catheter and the hub whereby, when the needle is within the operative member, the pointed stylet distal end of the needle and the tapered catheter form a continuous exterior surface for piercing the chest of a patient so that the needle and operative member are adapted to be inserted and the needle is then adapted to be removed for allowing the operative positioning of the catheter inside a patient and the hub and one way flutter valve outside the patient;

providing a cap fabricated of a transparent plastic material and having a cylindrical distal section of a reduced diameter and a length to encompass a minor portion of the needle and a major portion of the catheter when coupled, the cap having a cylindrical proximal section of an enlarged diameter and a length to encompass a major portion of the hub and a minor portion of the needle adjacent to the handle in abutment with the handle, the cap having a conical section coupling the proximal and distal sections encompassing portions of the needle and the hub and the catheter;

with the needle positioned within the catheter, and the distal end of the needle extending beyond the distal end of the catheter, inserting the catheter between a second rib and a third rib of a patient suffering from tension pneumothorax until the distal end of the catheter is in a pleural space;

withdrawing the needle from the catheter thereby creating an air passageway between the distal end of the catheter and proximal end of the catheter; and unrolling the flutter valve from the hub whereby, when there is no positive air pressure at the distal end of the catheter, the proximal end of the catheter will be covered by the flutter valve at an angle of about 45 degrees with respect to an imaginary plane perpendicular to the axis of the catheter and hub to preclude the escape of air through the catheter; and, whereby when there is positive air pressure at the distal end of the catheter there will be a passageway for air from the distal end of the catheter through the catheter and through the flutter valve to allow the escape of air through the catheter and through the flutter valve.

* * * * *